United States Patent [19]

Ayer

[11] Patent Number: 4,609,374

[45] Date of Patent: Sep. 2, 1986

[54] OSMOTIC DEVICE COMPRISING MEANS FOR GOVERNING INITIAL TIME OF AGENT RELEASE THEREFROM

[75] Inventor: Atul D. Ayer, Mt. View, Calif.

[73] Assignee: ALZA Corporation, Palo Alto, Calif.

[21] Appl. No.: 725,961

[22] Filed: Apr. 22, 1985

[51] Int. Cl.⁴ .................................................. A61K 9/22
[52] U.S. Cl. ........................................ 604/892; 424/19
[58] Field of Search .................. 604/890, 891–897; 424/19, 20, 21, 28

[56] References Cited

U.S. PATENT DOCUMENTS

| | | | |
|---|---|---|---|
| 4,449,983 | 5/1984 | Cortese et al. | 604/892 |
| 4,455,143 | 6/1984 | Theeuwes et al. | 604/890 |
| 4,522,625 | 6/1985 | Edgren | 604/892 |

Primary Examiner—John D. Yasko
Attorney, Agent, or Firm—Paul L. Sabatine; Edward L. Mandell; Steven F. Stone

[57] ABSTRACT

An osmotic dispensing device is disclosed for delivering a medicine to a biological environment of use. The device comprises a semipermeable wall surrounding a compartment with an osmotic passageway in the semipermeable wall connecting the outside of the device with the compartment. The compartment house a medicine releasably held on a carrier member selected from the group consisting of cellulose esters, cellulose ethers and cellulose ester-ethers.

8 Claims, 2 Drawing Figures

4,609,374

OSMOTIC DEVICE COMPRISING MEANS FOR GOVERNING INITIAL TIME OF AGENT RELEASE THEREFROM

FIELD OF THE INVENTION

The present invention pertains to both a novel and useful osmotic device for dispensing a therapeutically effective amount of a beneficial agent. More particularly, the invention concerns an osmotic device comprising a compartment containing a beneficial agent carried by means for governing the initial time of release of the beneficial agent from the osmotic device.

BACKGROUND OF THE INVENTION

Osmotic devices for delivering a beneficial agent including a medicine to an environment of use are known to the prior art in U.S. Pat. No. 3,845,770, issued to Theeuwes and Higuchi, and in U.S. Pat. No. 3,916,899 issued to the same patentees. The osmotic devices disclosed in these patents comprise a compartment containing a beneficial agent including a medicine. The semipermeable wall is permeable to the passage of an external fluid and it is substantially impermeable to the passage of the beneficial agent including medicine. An osmotic passageway is provided through the wall for delivering the beneficial agent from the device. These prior art osmotic devices release the beneficial agent by imbibing fluid through the semipermeable wall into the compartment to form in the device an aqueous solution containing the beneficial agent that is dispensed through the passageway from the device. The external fluid is imbibed through the semipermeable wall into the compartment in a tendency towards osmotic equilibrium at a rate determined by the permeability of the semipermeable wall and the osmotic pressure gradient across the wall. These devices are extraordinarily effective for delivering an agent that is soluble in the fluid and exhibits an osmotic pressure gradient across the semipermeable wall against the external fluid, and for delivering an agent that has limited solubility in the fluid and is admixed with an osmotically effective osmagnet that is soluble in the fluid and exhibits an osmotic pressure gradient across the semipermeable wall against the fluid. The agent is incorporated into these devices during manufacture, prior to forming the semipermeable wall around the compartment. These prior art osmotic devices generally contained a large amount of a beneficial agent, and they operate successfully for delivering the beneficial agent to the environment of use.

The devices commence to deliver the beneficial agent as soon as the external fluid is imbibed through the semipermeable wall to form a solution containing the beneficial agent that is osmotically pumped from the device. The presently available osmotic delivery devices, when used in the fields of medicine and pharmacy for orally delivering a beneficial medicine to the stomach of a gastrointestinal tract, commence to dispense the beneficial medicine as soon as the osmotic device enters the fluid-rich environment of the stomach.

OBJECT OF THE INVENTION

It is an immediate object of this invention to provide a novel osmotic dispensing device for dispensing a beneficial agent to produce a beneficial effect, which dispensing device satisfies the shortcomings associated with the prior art dispensing osmotic devices.

It is another object of this invention to provide an osmotic delivery device that delays the onset of delivery of a beneficial agent from the device to an agent-receptor environment of use.

It is another object of this invention to provide an osmotic delivery system that delays the onset of agent release from the osmotic system for a period of time that approximately corresponds to the time needed for the osmotic system to pass through the stomach and enter the small intestine.

It is another object of this invention to provide an oral, osmotic delivery system for dispensing a beneficial agent including a medicine to the small intestine of the gastrointestinal tract of a warm-blooded animal for both topical and systemic therapy.

It is another object of this invention to provide an improvement in an osmotic device comprising a semipermeable wall surrounding a compartment, wherein the compartment contains a dosage unit amount of an orally administrable beneficial medicine carried on a nontoxic, nonswellable, inert carrier.

Another object of this invention is to provide an osmotic device that (a) houses a beneficial medicine coated onto an inert core possessing a water-sorption property, which core takes up water that enters the device, and (b) releases the beneficial medicine after the core becomes substantially saturated with water, thereby (c) delaying the onset of release of beneficial agent from the osmotic device.

Another object of the invention is to provide a method of administering a beneficial medicine to a warm-blooded animal by orally admitting into the animal an osmotic device comprising a medicine supported and carried on an inert, compressed core that, when the osmotic device is in use, releases the beneficial medicine from the core at a controlled rate over a prolonged period of time.

Other objects, features, aspects and advantages of the invention will be more apparent to those versed in the dispensing art from the following detailed specification taken in conjunction with the drawing figures and the accompanying claims.

BRIEF DESCRIPTION OF THE DRAWINGS

In the drawings which are not drawn to scale, but are set forth to illustrate various embodiments of the invention, the drawing figures are as follows.

In the drawings and in the specifications like parts in related figures are identified by like numbers. The terms appearing earlier in the specification and in the description of the drawing figures, as well as embodiments thereof, are further detailed elsewhere in the disclosure.

DETAILED DESCRIPTION OF THE DRAWINGS

Figure 1:
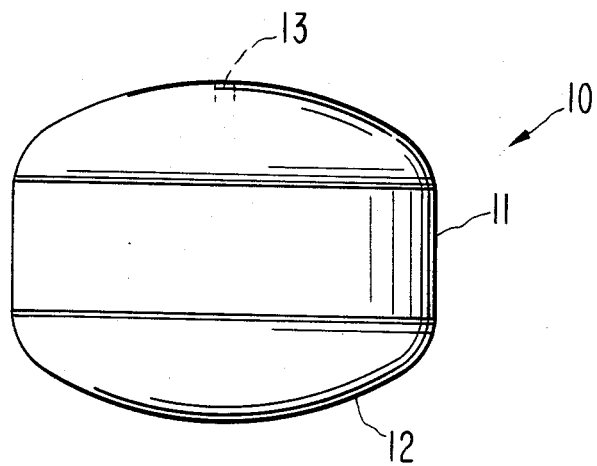
FIG. 1, is a view of an osmotic dispensing device designed for delivering a beneficial agent including a medicine to an environment of use such as the gastrointestinal tract of a warm-blooded animal.
Figure 2:
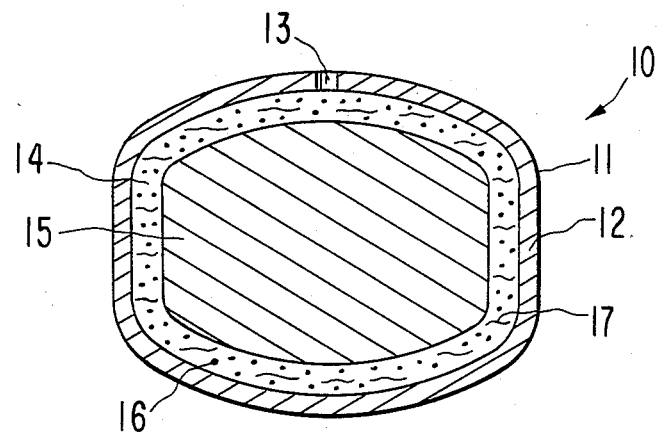
FIG. 2, is an opened view of the osmotic dispensing device of FIG. 1, with FIG. 2 illustrating the structural members of the osmotic dispensing device.

Turning now to the drawing figures in detail, which drawing figures are an example of an osmotic dispensing device provided by the invention, and which drawing figures are not to be construed as limiting, one example of an osmotic dispensing device is seen in FIGS. 1 and 2. In FIG. 1, osmotic device 10 is seen comprising a body member comprising a wall 12 that surrounds and forms an internal compartment not seen in FIG. 1. Osmotic dispensing device 10 is provided with an osmotic passageway 13 in wall 12, which which osmotic passageway 13 connects the exterior of osmotic device 10 with the interior of device 10.

In FIG. 2, osmotic dispensing device 10 is seen in opened section. In FIG. 2, osmotic device 10 comprises body 11, wall 12, osmotic passageway 13 and internal compartment 14. Wall 12 is formed of a nontoxic polymeric composition that is totally, or in at least a part, permeable to the passage of an external fluid and it is substantially impermeable to the passage of a beneficial agent including medicine. The polymeric composition forming wall 12 is inert and it maintains its physical and chemical integrity during the dispensing life of osmotic device 10.

Internal compartment 14 houses an inner core 15. Core 15 can have any geometric shape that permits its housing inside compartment 14. Core 15 in one example possesses a shape that corresponds to the interior shape of osmotic device 10. Core 15 is a carrier means for beneficial agent 16, represented by dots. As a carrier means, core 15 occupies an area inside compartment 14 that is smaller than the inside area of compartment 14, thereby providing space for core 15 to serve as a physical vehicle or physical support for a dosage unit amount of beneficial agent 16, which includes a medicine.

Core 15, in one presently preferred embodiment, is a carrier means for providing a surface that serves as a vehicle for carrying small amounts of beneficial agent 16. Core 15 is a carrier for small amounts of a beneficial agent 16, usually from 10 nanograms to 125 milligrams of beneficial agent 16, serves to limit the space available for diluting beneficial agent 16 with fluid imbibed through wall 12 into compartment 14. The use of core 15 in this embodiment, thereby prolongs the zero order rate of release of beneficial agent 16 from osmotic device 10.

In another presently preferred embodiment, core 15 additionally is a means for delaying the onset of release of beneficial agent 16 from osmotic device 10. In this capacity, core 15 is formed of at least one material that exhibits a fluid-sorptive property, mainly a water-sorptive property. Core 15 sorption process embraces fluid sorbed by core 15 until core 15 is substantially saturated with absorbed fluid. Then, beneficial agent 16 is released from core 15 for delivery from osmotic device 10. The delay of onset of release of beneficial agent 16 from core 15 corresponds approximately to the time required by the penetrant fluid to substantially saturate core 15.

Beneficial agent 16, as represented by dots, and supported on carrier means 15, can be from insoluble to very soluble in an aqueous-type fluid, which includes biological fluid that enters osmotic device 10. Beneficial agent 16 when soluble in the fluid, exhibits an osmotic pressure gradient across wall 12 against an external fluid that is imbibed into compartment 14. When the beneficial agent has limited solubility in the external fluid it can be mixed with an osmagent 17 and coated onto carrier means 15. In this embodiment osmagent 17 is soluble in the external fluid and it exhibits an osmotic pressure gradient across wall 12 against the external fluid. In operation device 10 containing beneficial agent formulation 16 releases said formulation by fluid being imbibed into compartment 14 in a tendency towards osmotic equilibrium at a rate determined by the permeability of wall 12 and the osmotic pressure gradient across wall 12. The imbibed fluid continuously forms a solution containing the active agent, or a solution of osmagent containing active agent in suspension, which solution in either instance is released by the combined operation of device 10. These operations include the solution being osmotically and hydrodynamically delivered through passageway 13 to the biological environment of use.

FIGS. 1 and 2 depict one presently preferred embodiment of osmotic device 10. In this embodiment device 10 is made for oral use, that is, for releasing a locally acting medicine, or a systemically acting medicine in the gastrointestinal tract. The oral system can have various shapes and sizes. In one design, device 10 can be curved, such as round, with a diameter of $\frac{1}{8}$ inch to 9/16 inch, or it can be shaped like a capsule having a range of sizes from triple zero to zero, and from 1 to 8.

While FIGS. 1 and 2 illustrate one dispensing device that can be made according to the invention, it is to be understood device 10 can take a wide variety of shapes, sizes and forms for delivering a beneficial agent including a medicine to the environment of use. For example, the osmotic devices include buccal, implant, artificial gland, cervical, intrauterine, nose and the like osmotic devices. In these forms device 10 can be adapted for administering a beneficial medicine to numerous animals, warm-blooded mammals, humans, avians and reptiles. The device also can be sized, shaped, structured and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, chemical reactions and other environments of use.

DETAILED DESCRIPTION OF THE INVENTION

In accordance with the practice of the invention, it now has been found that osmotic delivery device 10 can be manufactured with a wall 12 formed of a material that does not adversely affect beneficial agent 16, which includes drug, an osmagent, an animal, or a host. Wall 12 is formed of polymeric composition permeable to the passage of an external aqueous-type fluid such as water and biological fluids, while remaining essentially impermeable to the passage of beneficial agent 16 which includes drug, osmagent, and the like. The selectively semipermeable materials forming wall 12 are insoluble in fluids, and they are non-erodible, hence they maintain their physical and chemical integrity during the operation of the osmotic device in the environment of use.

Typical materials for forming wall 12 include semipermeable polymers known to the art as osmosis and reverse osmosis membranes. These include cellulose ester, cellulose ether, cellulose ester-ether, cellulose acylate, cellulose diacylate, cellulose triacylate, cellulose acetate, cellulose diacetate, cellulose triacetate, agar acetate, amylose triacetate, beta glucan acetate, cellulose acetaldehyde dimethyl acetate, cellulose acetate ethyl carbamate, cellulose acetate methyl carbamate, cellulose acetate succinate, cellulose acetate dimethylaminoacetate, cellulose acetate ethyl carbamate, cellulose acetate chloroacetate, cellulose dipalmate, cellulose dioctanoate, cellulose dicaprylate, cellulose dipentanlate, cellulose acetate valerate, cellulose acetate succinate, cellulose propionate succinate, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; lightly cross-linked semipermeable polystyrene derivative, cross-linked semipermeable poly(sodium styrene sulfonate), semipermeable poly(vinylbenzyltrimethylammonium chloride), cellulose acetate having a degree of substitution up to 1 and an acetyl content up to 21%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020. Generally, semipermeable materials useful for forming wall 12 will have a fluid permeability of $10^{-5}$ to $10^{-1}$ (cc mil/cm$^2$ hr/atm) expressed per atmosphere of hydrostatic or osmotic pressure difference across semipermeable wall 12 can be used for the intended purpose.

The expression core 15 as used for the purpose of this invention, and its equivalent expression core means and carrier means generically denote a material or a composition of matter, which in all its embodiments is nontoxic, non-therapeutic, inert and substantially maintains a constant area or volume during the period of time osmotic device 10 is in the environment of use. The term non-therapeutic means core 15 is free of physiological and pharmacological properties. The expression constant area denotes core 15 is non-expandable and it does not substantially increase in dimensions in the presence of the absorbed fluid. Typical materials for forming core 15 include a member selected from the group consisting of a cellulose ester, cellulose ether, cellulose ester-ether, cellulose acylate, cellulose diacylate, cellulose triacylate, cellulose acetate, cellulose diacylate, cellulose triacylate, cellulose acetate, cellulose diacylate, cellulose triacetate, cellulose triacetate having an acetyl content of 32%, cellulose acetate having an acetyl content of 39.8%, cellulose triacetate having an acetal content of 43.5%, hydroxypropyl cellulose, hydroxypropyl methylcellulose, hydroxyethyl cellulose, methylcellulose, ethylcellulose, and the like. The core can contain a fluid absorbing agent such as polyethylene glycol, and the like.

Core member 15 comprises a multiplicity of granules of a core forming composition that is compressed under a pressure head of from 0.5 to about 5 tons into a unit mass that is then coated with beneficial agent formulation 16. Core member 15 can be a single member such as a preshaped, precut section of polymer as set forth above, which core-forming polymer then is coated with a beneficial agent formulation 16.

Those skilled in the art can readily determine the sorption property of a material, or a blend of materials suitable for the particular core application. Various techniques can be used to determine the water-sorption properties, and the time required for different materials to reach saturation. One technique that has been found to be suited is the increase in weight procedure. In the weight procedure, a core-forming material is submerged in a fluid and weighed at periodic intervals until a constant weight is obtained for the core-forming material. Another procedure used for this purpose is the buoyant procedure that compares the water absorbed to the volume of water displayed by comparing the volume and weight. Procedures for determining fluid-sorption are recorded in *Annual Book of ASTM Standards*, Section 8, pp 208–211, 584–587, published in 1984 by ASTM, Philadelphia, PA; and in *Encyclopedia of Polymer Science and Technology*, Vol. 12, pp 679–700, published in 1970 by John Wiley & Sons, Inc., New York.

Additional scientific criterions that can be used by those versed in the art for selecting core-forming materials that are inert and exhibit varying sorption properties include the following: (a) polymeric compositions having a high degree of substitution, for example, the material has undergone esterification or etherification particularly acylation towards or to completion and thereby demonstrates a decreased fluid-sorption; (b) the core forming material exhibits a fluid-sorption decrease with increasing molecular size of its substituting groups, such as ether or ester; (c) the core-forming material exhibits a fluid-sorption decrease proportional to the increase in size of the substituents; for example, the decrease occurs as the number of carbon atoms increase in a hydrocarbon moiety such as an alkyl or alkoxy moiety; (d) the core-forming material exhibits a decrease fluid-sorption with an increase in the number of hydrophobic ether and larger hydrophobic ester groups and with an accompanying decrease in the number of hydrophilic ether and hydrophilic ester groups; and, (e) the core-forming material exhibits a decrease fluid-sorption as the number of polar, ionic groups decrease.

The expression beneficial agent and beneficial medicine formulation as used herein denotes a beneficial drug neat, and a composition comprising a beneficial drug and an osmagent. In the specification and the accompanying claims, the term medicine includes drug, and the term drug includes any physiologically or pharmacologically active substance that produces a local or systemic effect in animals, including warm-blooded mammals; humans and primates; fishes; reptiles, farm, sport and zoo animals. The term 'physiologically' as used herein denotes the administration of a drug to produce normal levels and functions. The term 'pharmacologically' denotes variations in response to amount of drug administered to the host. *Stedman's Medical Dictionary*, 1966, published by Williams and Wilkins, Baltimore, MD. The active drug that can be delivered includes inorganic and organic drugs without limitations, those drugs that act on the central nervous system, depressants, hypnotics, sedatives, psychic energizers, tranquilizers, anticonvulsants, muscle relaxants, anti-parkinson agents, analgesics, anti-inflammatory, local anesthetics, muscle contractants, anti-microbials, anti-malarials, hormonal agents, contraceptives, sympathomimetics, diuretics, anti-parasitics, neo-plastics, hypoglycemics, ophthalmics, electrolytes, diagnostic agents and cardiovascular drugs. The amount of medicine carried, coated or compressed onto core means generally is from 0.1 mg to 125 mg of medicine, of course, lower and higher amounts in those embodiments are within the scope of the invention.

Exemplary drugs that can be carried on the core member and delivered by the osmotic device of this invention include prochlorperazine edisylate, prochlorperazine maleate, prazosin hydrochloride, lonidine hydrochloride, hydralazine hydrochloride, dextromethorpan hydrobromine, dextroamphetamine phosphate, diethylpropionm hydrochloride, isoxsuprine hydrochloride, ambenonium chloride, phenoxybenzamine hydrochloride, phentolamine hydrochloride, guanethidine sulfate, clidinium bromide, glycopyrrolate, homatropine methylbromide, hyoscyamine hydrobromide, mepenzolate bromide, methscopolamine bromide, balofen, and the like. These drugs and their daily dose are known to the art in *Pharmaceutical Sciences,* by Remington, 16th Ed., 1980, published by Mack Publishing Company, Easton, PA.

The medicine can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate and salicylate. For acid medicine, salts of metals, amines or organic cations, for example, quaternary ammonium can be used. Derivatives of medicine such as esters, ethers and amides can be used. Also, a medicine that is water insoluble can be used in a form that is a water soluble derivative thereof to serve as a solute and, on its release from the devices, it is converted by enzymes, hydrolyzed by body pH or other metabolic process to the original biologically active form.

The osmagent present in osmotic device 10, when used according to the mode of the invention, are osmotically effective compounds soluble in fluid that enter the device and exhibit an osmotic pressure gradient across the semipermeable wall against the exterior fluid. Osmotically effective osmagents useful for the present purpose include magnesium sulfate, magnesium chloride, sodium chloride, lithium chloride, potassium sulfate, sodium carbonate, sodium sulfite, lithium sulfate, potassium chloride, sodium sulfate, d-mannitol, urea inositol, raffinose, glycose, mixtures thereof, and the like. The osmagent is usually present in an excess amount, and it can be in any physical forms, such as particle, powder, granule, and the like. The osmotic pressure in atmospheres, atm, of the osmagents suitable for the invention will be greater than zero atm, generally from zero atm up to 500 atm, or higher. The osmotically effective compounds are known to the art in U.S. Pat. Nos. 4,177,256 and 4,449,983.

The solubility of a medicine in the fluid that enters the compartment can be determined by known techniques. One method consists of preparing a saturated solution comprising the fluid plus the medicine as ascertained by analyzing the amount of medicine present in a definite quantity of the fluids. A simple apparatus for this purpose consists of a test tube of medium size fastened upright in a water bath maintained at constant temperature and pressure, in which the fluid and medicine are placed and stirred by a rotating glass spiral. After a given period of stirring, a weight of the fluid is analyzed and the stirring continued an additional period of time. If the analysis shows no increase of dissolved medicine after successive periods of stirring, in the presence of excess solid medicine in the fluid, the solution is saturated and the results are taken as the solubility of the product in the fluid. If the medicine is soluble, an added osmotically effective compound optionally may not be needed. If the medicine has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin,* No. 67 of the Hygenic Laboratory; *Encyclopedia of Science and Technology,* Vol. 12. pp 542-556, 1971, published by McGraw-Hill, Inc.; and, *Encyclopedia Dictionary of Physics,* Vol. 6, pp 547-557, 1962, published by Pergammon Press, Inc.

The expression osmotic passageway as used herein comprises means and methods suitable for releasing a beneficial agent including a medicine from compartment 14. The osmotic passageway or orifice will pass through the wall for communicating with compartment 14. The expression passageway includes aperature, orifice, bore, pore, porous element through which a beneficial agent can migrate, hollow fiber, capillary tube, and the like. The expression also includes a material that erodes in the environment of use to produce a passageway in the device. Representative materials suitable for forming a passageway include an erodible poly(glycolic) and poly(lactic) acids in the wall, gelatinous filaments, poly(vinyl alcohol), and the like. The passageway can be formed by leaching a material such as sorbitol from the wall. The passageway can have any shape. For example, round, triangular, square, elliptical, irregular, and the like. Also, the device can be constructed with one or more passageways. In an embodiment when the device is fabricated with more than one passageway they can be construed as the functional equivalent in an operative embodiment of a single osmotic passageway. The expression osmotic passageway includes passageways formed by mechanical drilling or laser drilling through the wall. Generally, for the purpose of this invention, the passageway will have a maximum cross-sectional area, A, defined by equation 1:

$$\frac{L}{F} \times \frac{Qv}{t} \times \frac{1}{DS} \quad (1)$$

wherein L is the length of the passageway, (Qv/t) is the mass delivery rate of the agent D released per unit of time, D is the diffusion coefficient of the medicine in the release solution, S is the solubility of the medicine in the fluid and F has a value of approximately 2 to 1000, said osmotic passageway having a minimum area, $A_s$, defined by equation 2:

$$\left[ \frac{Lv}{t} \times 8 \times \frac{\pi \eta}{\Delta p} \right] /12 \quad (2)$$

wherein L is the length of the passageway, v/t is the volume of the medicine released per unit of time, $\pi$ is 3.14, $\eta$ is the viscosity of the solution being released, and $\Delta P$ is the hydrostatic pressure difference between the inside and the outside of the compartment and having a value up to 20 atm. The dimension for the osmotic passageway is disclosed in U.S. Pat. No. 3,916,899. Laser drilling equipment having photo detection means for orienting a device for surface selected drilling are known in U.S. Pat. No. 4,063,064 and U.S. Pat. No. 4,088,864.

The osmotic device of the invention is manufactured using standard machines. For example, in one embodiment a plurality of core forming particles are compressed under a pressure head up to 50 tons into a solid, compacted mass and then coated with a medicine. In another embodiment, a polymer is cut into a shape corresponding to the shape of a compartment of an osmotic device and then the shaped and sized core member is coated with a medicine formulation. In another embodiment a medicine and an osmagent, and optionally other ingredients that may be housed in the compartment of an osmotic device, are blended to form a homogeneous composition and then pressed onto a solid core possessing dimensions that correspond to the internal dimensions of the area to be occupied in the compartment. The various ingredients can be mixed with a solvent by ballmilling, calendering, stirring or rollmilling, and then pressed onto the preselected shaped core. In another manufacture the medicine can be coated by dipping or air suspension coating onto the core member. The semipermeable wall can be applied around the medicine core by molding, spraying or dipping the medicine coated, pressed shapes into a wall forming material. Another presently preferred technique that can be used for applying the wall is the air suspension procedure. This procedure consists in suspending and tumbling the medicine coated core in a current of air and a wall forming composition until the wall is applied to the composite. The air suspension procedure is described in U.S. Pat. No. 2,779,241. *J. Am. Pharm. Assoc.*, Vol. 48, pp 451–459, 1979, and ibid., Vol. 49, pp 82–84, 1960. Other standard manufacturing procedures are described in *Modern Plastics Encyclopedia,* Vol. 46, pp 62–70, 1969; and in *Pharmaceutical Sciences,* by Remington, 14th Ed., pp 1626–1678, published by Mack Publishing Company, Easton, PA.

Exemplary solvents suitable for manufacturing the wall and the core include inorganic and organic solvents that do not adversely harm the wall and the core forming material, and the final device. The solvents broadly include members selected from the group consisting of aqueous solvents, alcohols, ketones, esters, ethers, aliphatic hydrocarbons, halogenated solvents, cycloaliphatic aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethelene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene toluene, naptha, 1,4-dioxane, tetrahydrofuran, diglyme, water, and mixtures there of such as acetone and water, acetone and methanol, acetone and ethyl alcohol, methylene dichloride and methanol, and ethylene dichloride and methanol, and the like.

The following example illustrates means and methods for carrying out the present invention. The example is merely illustrative and it should not be considered as limiting the scope of the invention, as this example and other equivalents thereof will become more apparent to those versed in the dispensing art in the light of the present disclosure, the drawings and the accompanying claims.

EXAMPLE 1

As osmotic dispensing device for the controlled delivery of the beneficial medicine salbutamol at an osmotically controlled rate is manufactured as follows:

1. Inert core fabrication: First, cellulose acetate having an acetyl content of 39.8% was wet granulated with ethanol and hydroxypropyl methylcellulose. The wet granules were passed through a 20 mesh screen and oven dried for 14 hours at about 50° C. Next, the dried granules were passed through 30 mesh screen and the lubricating agent barium sulfate added to the granules. The granules were compressed under a pressure head of 8 tons into 5/16 inch standard concave, cores shaped for use in an osmotic device. The cores weighed 275 mg and had a hardness in excess of 30 kp.

2. Medicine formulation: Next, a medicine formulation for coating onto the inert cores was prepared by dissolving salbutamol sulfate in ethanol:water solvent. Then hydroxypropyl methylcellulose was added and the ingredients blended into a homogeneous blend. The blend was coated onto the cellulose acetate inert cores comprising the 39.8% acetyl content. The cores were coated in an air suspension machine until each core was surrounded with a uniform coat of sulbutamol sulfate. Laser drilling machines are commercially available from Coherent Radiation of California, and Photon Sources of Michigan.

3. Rate controlling semipermeable wall: First, cellulose acetate having an acetyl content of 39.8% was dissolved in a methylene chloride:methanol solvent. The inert cores with the salbutamol sulfate were surrounded with a cellulose acetate wall in the air suspension machine until each core-drug formulation was surrounded with a semipermeable wall. The osmotic dispensing devices were dried in a forced air oven for 48 hours at 50° C. to free the device of solvent. Then, an osmotic passageway was drilled through the semipermeable wall connecting the exterior of the osmotic device with the medicine formulation.

The osmotic device exhibited the following characteristics. The cellulose acetate core exhibited a 5% water-sorption rate. The salbutamol sulfate exhibited an osmotic pressure of 34 atm and a solubility in water of 265 mg/ml. The core weighed 275 mg and comprised 80 wt% cellulose acetate having an acetyl content of 39.8%, 4 wt% hydroxypropyl methylcellulose and 16 wt% barium sulfate. The semipermeable wall had an average thickness of 4 mil. The medicine boat on the inert core weighed 9 mg and comprised 83 wt% salbutamol sulfate and 17 wt% hydroxypropyl methylcellulose. The osmotic device exhibited a 2 hour delay in the onset of medicine delivery and delivered 0.4 mg per hour over a 14 hour period of time.

EXAMPLE 2

An inert core is made by wet granulating 4000 grams of cellulose acetate having an acetyl content of 43.3% and 200 grams of hydroxypropyl methylcellulose in an ethanol:water solvent. The wet granules are passed through a 20 mesh screen and dried for 14 hours at 50° C. Next, the dry granules are mixed with 800 grams of barium sulfate and the blended granules passed through a 30 mesh screen. The granules then are pressed into a core adapted, shaped and sized using a standard tabletting machine with a 7/16 inch diameter punch. The cores formed by this procedure weighed 625 mg.

Next, a medicine formulation for coating onto the inert cores is prepared by thoroughly dissolving 190 grams of potassium chloride and 47 grams of hydroxypropyl methylcellulose in 2133 millileters of distilled water. Then, the inert cores placed in an air suspension machine and each core was coated with 0.05 mg of the potassium chloride formulation.

Finally, a rate controlling semipermeable wall is placed around the medicine coated core. This procedure consists essentially of first dissolving 100 grams of cellulose acetate having an acetyl content of 39.8% in 1900 grams of methylene chloride:methanol solvent, (90:10 by weight). The inert cores coated with the potassium chloride are surrounded with a cellulose acetate wall in an air suspension machine until each core-drug formulation was surrounded with a semipermeable wall that weighed 35 mg. The osmotic dispensing devices next are dried in a forced air oven for 48 hours at 50° C., to free the devices of solvent. Then, an osmotic passageway is drilled through the semipermeable wall connecting the exterior of the device with the medicine formulation. The passageway has a diameter of 0.26 mm and the device has a rate of release of about 14 milligrams per hour.

EXAMPLE 3

An osmotic delivery device for the controlled delivery of the beneficial drug atropine sulfate an anticholinergic, is prepared as follows.

First, a formulation comprising 70% atropine sulfate, 25% hydroxypropyl methylcellulose and 5% polyvinyl pyrrolidone is dissolved in an inorganic solvent consisting essentially of methylene chloride:methanol, (60:40 by weight), to yield a coating solution containing 8% solids. Then, a plurality of cores, each weighing 255 mg having a diameter of ⅜ inch and made of cellulose acetate having an acetyl content of 20%, polyethylene glycol, hydroxypropyl methylcellulose and magnesium stearate are coated with the drug formulation in an air suspension machine. Next, the drug coated cores are surrounded with a semipermeable wall. The wall is formed from a wall-forming composition comprising cellulose acetate having an acetyl content of 39.8% dissolved in a solvent comprising methylene chloride:methanol, (90:10 by weight), to obtain a coating solution comprising 5% solid. Each core is surrounded with the semipermeable wall forming composition until the wall weighs about 18 mg. Finally, the osmotic devices are removed from the air suspension coater and dried in a forced air oven for 48 hours at 50° C. Then, after cooling to room temperature a 0.26 mm osmotic passageway is laser drilled through the semipermeable wall to yield the osmotic device having a delayed onset of delivery of atropine sulfate.

EXAMPLE 4

A non-stirring rate osmotic device that releases drug independent of the pH of the environment is manufactured by following the procedures described immediately above. In the present example, the cores consisted of 95% cellulose acetate, 2% ethyl cellulose, 1.5% magnesium stearate and 0.5% polyethylene glycol 4000. The compressed oval cores are coated with a medicinal formulation comprising 5.6% haloperidol, 25% hydroxypropyl methylcellulose, 5% polyvinyl pyrrolidone and 64.4% succinic acid dissolved in methylene chloride:methanol, (50:50 by volume), to obtain 3% solid. The cores are air coated with 1 mg of haloperidol over each core. The drug-core composite are surrounded with a semipermeable wall with the following wall-forming composition: 90% cellulose acetate having an acetyl content of 39.8%, 5% polyethylene glycol having an average molecular weight of 3350, and 5% hydroxypropyl methylcellulose dissolved in methylene chloride:methanol, (88:12 by weight), with a 4% solid composition. Each core is coated with a 26 mg semipermeable formulation wall. After drying, a 0.36 mm osmotic passageway is laser drilled in the semipermeable wall, to produce the osmotic device having a delayed onset of initial atropine haloperidol release.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modification, changes, additions and omissions in the system illustrated and described can be made without departing from the spirit of the invention.

I claim:

1. An osmotic dispensing device for delivering a beneficial medicine formulation to an environment of use, comprising:
   (a) a wall formed in at least a part of a semipermeable composition permeable to the passage of an exterior fluid present in the environment of use and substantially impermeable to the passage of the beneficial medicine formulation, the wall surrounding and forming;
   (b) a compartment;
   (c) means in the compartment for carrying a beneficial medicine formulation, said means formed of a nontoxic, physiologically and pharmacologically inert means-forming material selected from the group consisting essentially of a cellulose ester, cellulose ether, cellulose ester-ether, cellulose acylate, cellulose diacylate, cellulose triacylate, cellulose acetate, cellulose diacetate and cellulose triacetate;
   (d) a dosage unit amount of a medicine formulation carried on the means; and,
   (e) a passageway in the wall communicating with the compartment for delivering the beneficial medicine formulation from the osmotic device.

2. The osmotic dispensing device for delivering a beneficial medicine formulation to an environment of use according to claim 1, wherein the means is essentially insoluble in aqueous fluids.

3. The osmotic dispensing device for delivering a beneficial medicine formulation to an environment of use according to claim 1, wherein the medicine formulation carried on the means is releasably coated on the means.

4. The osmotic dispension device for delivering a beneficial medicine formulation to an environment of use according to claim 1, wherein the means is a compressed core.

5. The osmotic dispensing device for delivering a beneficial medicine formulation to an environment of use according to claim 1, wherein the means possesses a shape corresponding to the internal shape of the compartment.

6. The osmotic dispensing device for delivering a beneficial medicine formulation to an environment of use according to claim 1, wherein the means is shaped, sized and adapted for placement in the osmotic dispensing device.

7. A process for manufacturing an osmotic dispensing device for delivering a medicine to a fluid environment of use, the process comprising:
   (a) compressing at least one water insoluble, nontoxic inert material selected from the group consisting of cellulose ester, cellulose ether, cellulose ester-ether, cellulose acylate, cellulose diacylate and cellulose triacylate, into a solid, hard core;

(b) coating the compressed core with a first coat comprising a medicine formulation to form a medicine coated core;

(c) surrounding the medicine coated core with a semipermeable wall; and, (d) drilling a passageway in the wall connecting the exterior of the device with the interior of the device for releasing the medicine through the passageway from the device.

8. A method for delivering a medicinal formulation to a fluid environment of use, wherein the method comprises:

(a) admitting into the fluid environment of use an osmotic dispensing device comprising:

(1) a wall formed of a semipermeable composition permeable to the passage of fluid present in the environment of use and substantially impermeable to a medicinal formulation surrounding and defining:

(2) a compartment;

(3) means in the compartment for delaying the onset of initial medicine formulation release from the osmotic device, said means also a carrier support for a medicinal formulation;

(4) a medicinal formulation carried on the carrier means; and, (5) an osmotic calibrated passageway in the wall communicating the fluid environment with the compartment for releasing the medicine formulation from the device;

(b) imbibing fluid from the environment into the compartment to form a solution containing the medicine formulation and for sorption by the means;

(c) delivering the medicinal formulation from the device by releasing the medicinal formulation from the means and then through the passageway to the fluid environment of use.

* * * * *